United States Patent [19]

Lam

[11] Patent Number: 5,601,596
[45] Date of Patent: Feb. 11, 1997

[54] HAEMOSTATIC PRESSURE PAD

[76] Inventor: Anthony H. K. Lam, 10151 - 74 Street N.W., Edmonton, Alberta, Canada, T6A 2X8

[21] Appl. No.: 368,481

[22] Filed: Jan. 4, 1995

[51] Int. Cl.$^6$ .................................................. A61B 17/00
[52] U.S. Cl. ............................................................ 606/201
[58] Field of Search ................................. 606/201–203, 606/204

[56] References Cited

U.S. PATENT DOCUMENTS

| 1,561,116 | 11/1925 | Silliman. | |
|---|---|---|---|
| 2,234,961 | 3/1941 | Canada | 606/203 |
| 2,712,314 | 7/1955 | Kohl. | |
| 3,779,249 | 12/1973 | Semler. | |
| 4,314,568 | 2/1982 | Loving. | |
| 4,572,182 | 2/1986 | Royse. | |
| 5,021,057 | 6/1991 | Byrne, Jr. | 606/201 |
| 5,269,803 | 12/1993 | Geary et al. | |
| 5,304,201 | 4/1994 | Rice. | |
| 5,342,388 | 8/1994 | Toller | 606/201 |

FOREIGN PATENT DOCUMENTS 2447713  8/1980  France.

Primary Examiner—Michael Powell Buiz
Assistant Examiner—William Lewis

[57] ABSTRACT

A haemostatic pressure pad is described which includes a plinth-like body having a first finger portion and a second finger portion. The first finger portion has a first end and a second end. The second finger portion has a first end and a second end. The first finger portion and the second finger portion are conjoined at the respective second ends. The first finger portion is larger than the second finger portion. The plinth-like body has a contact face and an attachment face. A boss is positioned on the attachment face of the first finger portion for attaching the plinth-like body to an haemostatic compression device. A channel is positioned between the first finger and the second finger. The channel extends inwardly from the respective first ends of the first finger and the second finger, terminating at the conjoined respective second ends. The channel passes through the plinth-like body from the contact face to the attachment face.

6 Claims, 2 Drawing Sheets

HAEMOSTATIC PRESSURE PAD

FIELD OF THE INVENTION

The present invention relates to a haemostatic pressure pad intended to be used with a haemostatic compression device.

BACKGROUND OF THE INVENTION

Haemostatic pressure pads intended for use in a haemostatic compression device come in a variety of shapes and configurations. An example of a haemostatic pressure pad that is in common use is U.S. Pat. 4,572,182 which issued to Royse in 1986. The Royse patent discloses a haemostatic pressure pad which is a circular disk. The circular disk has a symmetrically positioned mounting boss and a "V" shaped notch. The mounting boss is used to mount the haemostatic pressure pad on an arterial clamp. The "V" shaped notch facilitates the placement of the haemostatic pressure pad over a catheter prior to removal of the catheter from a patient's artery.

None of the haemostatic pressure pads commercially available at the present time are capable of applying simultaneous pressure to both the femoral artery and the femoral vein.

SUMMARY OF THE INVENTION

What is required is haemostatic pad that is capable of applying simultaneous pressure to both the femoral artery and the femoral vein.

According to one aspect of the present invention there is provided a haemostatic pressure pad which includes a plinth-like body having a first finger portion and a second finger portion. The first finger portion has a first end and a second end. The second finger portion has a first end and a second end. The first finger portion and the second finger portion are conjoined at the respective second ends. The first finger portion is larger than the second finger portion. The plinth-like body has a contact face and an attachment face. Means are positioned on the attachment face of the first finger portion for attaching the plinth-like body to a haemostatic compression device. A channel is positioned between the first finger and the second finger. The channel extends inwardly from the respective first ends of the first finger and the second finger, terminating at the conjoined respective second ends. The channel passes through the plinth-like body from the contact face to the attachment face.

The haemostatic pressure pad, as described above, is capable of staunching blood flow from both a feboral artery and a feboral vein when used in accordance with the method that will hereinafter be further described. It is preferred that the channel have substantially parallel sidewalls. It is also preferred that an arrow be positioned on the attachment face #the first finger. The arrow extends away from the second finger substantially perpendicularly to the channel. This assists health care professionals in positioning the plinth-like body in accordance with the teachings of the method.

According to another aspect of the present invention there is provided a method of positioning a haemostatic pressure pad. Firstly, provide a haemostatic compression device. Secondly, provide a haemostatic pressure pad as described above. Thirdly, attach the haemostatic pressure pad to the haemostatic compression device. Fourthly, position the contact face of the haemostatic pressure pad on a leg of a patient with the wound positioned between the sidewalls of the channel.. The haemostatic compression device is used to apply sufficient force to staunch blood flow. The channel extends substantially perpendicularly to both a femoral artery and a femoral vein in the leg of the patient with the first finger staunching blood flow from the femoral artery and the second finger staunching blood flow from the femoral vein.

In order to ensure the intended positioning it is preferred that the haemostatic pad have an indicator arrow on the attachment face perpendicular to the channel. The health care professional is then able to ensure correct positioning merely by pointing the arrow toward the patient's umbilicus.

According to another aspect of the present invention there is provided an haemostatic compression device/haemostatic pad combination. The haemostatic compression device has a piston with a key shaped terminus. The haemostatic pressure pad, as described above, has an added feature of a boss having a key hole shaped aperture positioned on the attachment face of the first finger portion. The key shaped terminus of the piston from the haemostatic compression device is insertable into the key hole shaped aperture to attach the plinth-like body to an haemostatic compression device.

Other types of haemostatic pads are attached to a piston of an haemostatic compression device in such a manner that they are free to rotate. However, in accordance with the teachings of the method a particular positioning of the haemostatic pad is preferred. It is, therefore, preferable that the haemostatic pad be non-rotatably mounted. The combination, as described above, achieves that objective through the use of the key to key hole engagement.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
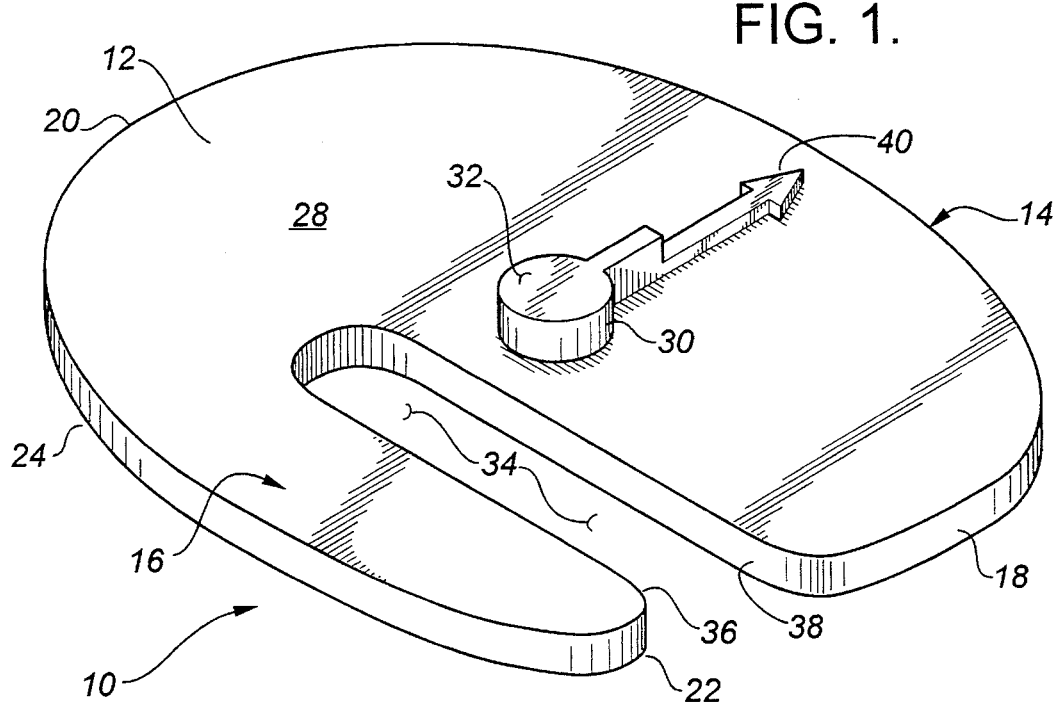
FIG. 1 is a perspective view of a haemostatic pad constructed in accordance with the teachings of the present invention.

The preferred embodiment, a haemostatic pressure pad generally identified by reference numeral 10, will now be described with reference to FIG. 1 through 5.

The primary procedure for which a haemostatic compression device is used is catheterization via a femoral artery or vein. One example of an instance in which catheterization would be used in when a patient is experiencing cardiogenic shock. A catheter is introduced through puncture wounds in the leg into a femoral artery, a femoral vein, or both. Often a hollow sheath, termed an "introducer" is placed into the puncture wound in the leg as a preliminary step. The catheter is extended through the introducer, along the artery (or vein)

and into the patient's heart. Haemostatic pressure pad 10 is intended for use in such procedures.

Figure 2:
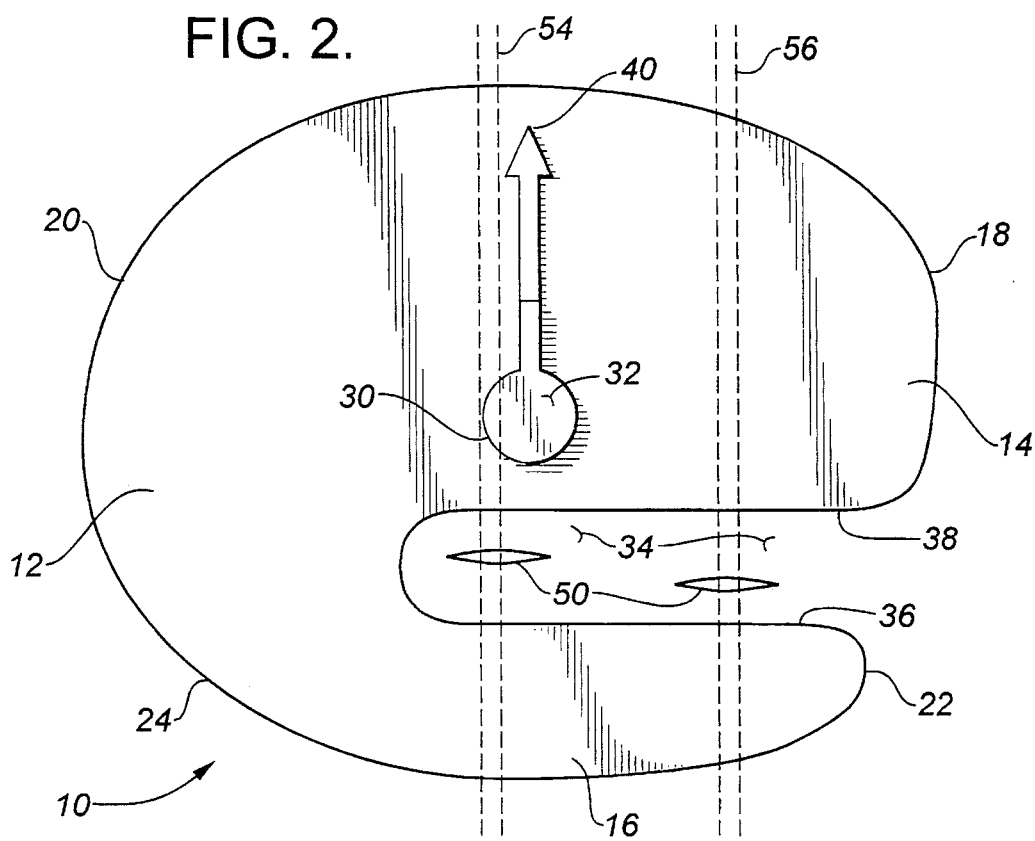
FIG. 2 is top plan view of the haemostatic pad illustrated in FIG. 1.
Figure 3:
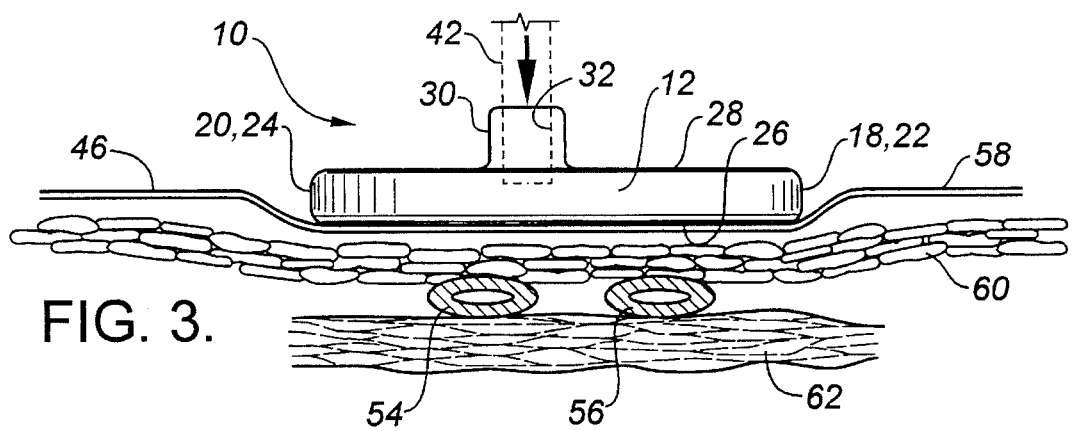
FIG. 3 is side elevation view of the haemostatic pad illustrated in FIG. 1.
Figure 5:
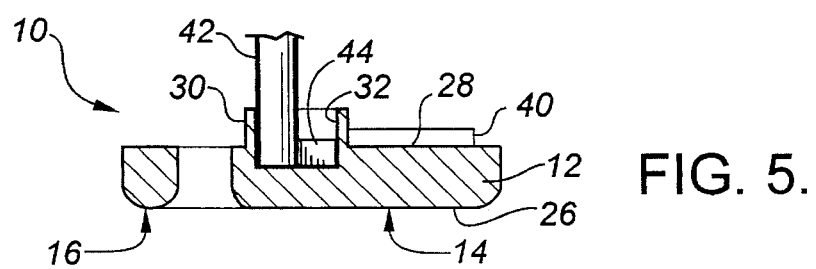
FIG. 5 is a side elevation view of the haemostatic pad illustrated in FIG. 1 in combination with an haemostatic compression device.

Referring to FIGS. 1 and 2, haemostatic pressure pad 10 includes a plinth-like body 12 including a first finger portion 14 and a second finger portion 16. First finger portion 14 has a first end 18 and a second end 20. Second finger portion 16 has a first end 22 and a second end 24. First finger portion 14 and second finger portion 16 are conjoined at respective second ends 20 and 24. First finger portion 14 is larger than second finger portion 16. The reason for this difference in size will become apparent from the description of use and operation. The blood flow through a femoral artery is from the heart to the leg. The blood flow through a femoral vein is from the leg to the heart. The pressure in the femoral artery is much greater that the pressure in the femoral vein and, therefore, a larger first finger portion is required. Referring to FIGS. 3 and 5, plinth-like body 12 has a contact face 26 and an attachment face 28. Referring to FIG. 1 and 2, a boss 30 having a key hole shaped aperture 32 is positioned on attachment face 28 of first finger portion 14 of plinth-like body 12. A channel 34 having substantially parallel sidewalls 36 and 38 is positioned between first finger portion 14 and second finger portion 16. Channel 34 extends inwardly from respective first ends 18 and 22 of first finger portion 14 and second finger 16, terminating at conjoined respective second ends 20 and 24. Channel 34 passes through plinth-like body 12 from contact face 26 to attachment face 28. An arrow 40 is positioned on attachment face 28 of first finger portion 14 of plinth-like body 12. Arrow 40 extends away from second finger portion 16 substantially perpendicularly to channel 34. This assists health care professionals in positioning plinth-like body 12 as will hereinafter be described in relation to the preferred method.

Referring to FIG. 5, it is preferred that haemostatic pressure pad 10 be used in combination with an haemostatic compression device having a piston 42 with a key shaped terminus 44. Key shaped terminus 44 of piston 42 from the haemostatic compression device is insertable into key hole shaped aperture 32 of boss 30 to attach plinth-like body 12 to the haemostatic compression device.

Figure 4:
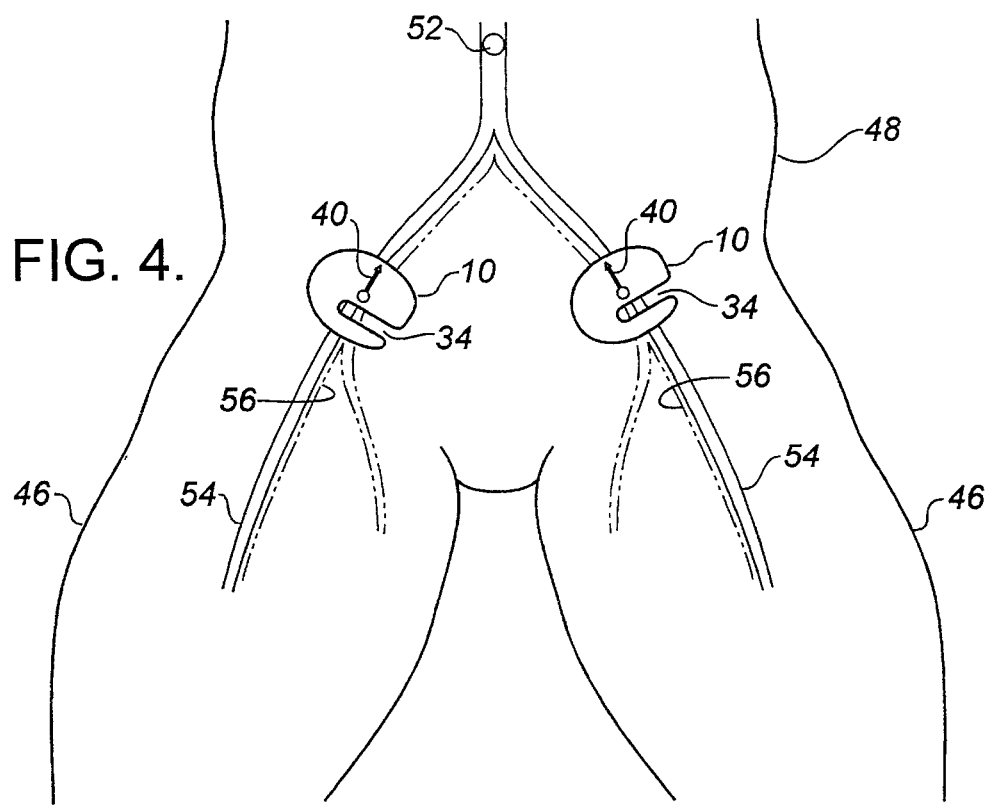
FIG. 4 is top plan view of the haemostatic pad illustrated in FIG. 1, positioned in accordance with the teachings of the preferred method.

Referring to FIG. 4, the preferred method of positioning haemostatic pressure pad 10 will now be described. It will be understood that preparatory steps would include: providing an haemostatic compression device; providing a form of haemostatic pressure pad 10; and attaching haemostatic pressure pad 10 to the haemostatic compression device.

Referring to FIG. 3, contact face 26 of haemostatic pressure pad 10 is placed in contact with a leg 46 of a patient 48. Referring to FIG. 4, puncture wounds 50 is positioned between sidewalls 36 and 38 of channel 34. Arrow 40 is positioned so that it points toward an umbilicus 52 of patient 48. Referring to FIG. 3, piston 42 of the haemostatic compression device is used to apply sufficient force to haemostatic pressure pad 10 to staunch blood flow. Referring to FIGS. 2 and 4, channel 34 extends substantially perpendicularly to both a femoral artery 54 and a femoral vein 56 in leg 46 of patient 48. When positioned as described first finger portion 14 staunches blood flow from femoral artery 54 and second finger portion 16 staunches blood flow from femoral vein 56. Referring to FIG. 3, in order to staunch the blood flow from femoral artery 54 and femoral vein 56, haemostatic pressure pad 10 must exert a force upon skin 58, and a subcutaneous layer of fat 60. Femoral artery 54 and femoral vein 56 are positioned between subcutaneous layer of fat 60 and muscle 62.

It will be apparent to one skilled in the art that modifications may be made to the illustrated embodiment without departing from the spirit and scope of the invention as hereinafter defined in the claims. The use of arrow 40 is preferred, but is not absolutely essential. Similarly, the use of boss 30 with key hole shaped aperture 32 is preferred, but is not absolutely essential.

The embodiments of the invention in which an exclusive property or privilege is claimed are defined as follows:

1. A haemostatic pressure pad, comprising:

a plinth-like body including a first finger portion having a first end and a second end, a second finger portion having a first end and a second end, the first finger portion and the second finger portion being conjoined at the respective second ends, the first finger portion being larger than the second finger portion, the plinth-like body having a contact face and an attachment face;

a boss having a key hole shaped aperture positioned on the attachment face of the first finger portion, such that a piston from an haemostatic compression device is insertable into the key hole shaped aperture to attach the plinth-like body to an haemostatic compression device;

a channel having substantially parallel sidewalls positioned between the first finger portion and the second finger portion, the channel extending inwardly from the respective first ends of the first finger portion and the second finger portion and terminating at the conjoined respective second ends, the channel passing through the plinth-like body from the contact face to the attachment face; and an arrow positioned on the attachment face of the first finger portion, the arrow extending away from the second finger portion substantially perpendicularly to the channel, thereby assisting health care professionals in positioning the plinth-like body.

2. A method of positioning a haemostatic pressure pad, comprising the following steps:

firstly, providing an haemostatic compression device;

secondly, providing a haemostatic pressure pad having a plinth-like body including a first finger portion having a first end and a second end, a second finger portion having a first end and a second end, the first finger portion and the second finger portion being conjoined at the respective second ends, the first finger portion being larger than the second finger portion, the plinth-like body having a contact face and an attachment face;

means positioned on the attachment face of the first finger portion for attaching the plinth-like body to an haemostatic compression device; and a channel having substantially parallel sidewalls positioned between the first finger portion and the second finger portion, the channel extending inwardly from the respective first ends of the first finger portion and the second finger portion and terminating at the conjoined respective second ends, the channel passing through the plinth-like body from the contact face to the attachment face;

thirdly, attaching the haemostatic pressure pad to the haemostatic compression device;

fourthly, positioning the contact face of the haemostatic pressure pad on a leg of a patient with the wound positioned between the sidewalls of the channel and using the haemostatic compression device to apply sufficient force to staunch blood flow, the channel extending substantially perpendicularly to both a femoral artery and a femoral vein in the leg of the patient with the first finger portion staunching blood flow from heart through the femoral artery and the second finger portion staunching blood flow along the femoral vein back to the heart.

3. A method of positioning a haemostatic pressure pad, comprising the following steps:

firstly, providing an haemostatic compression device;

secondly, providing a haemostatic pressure pad having
- a plinth-like body including a first finger portion having a first end and a second end, a second finger portion having a first end and a second end, the first finger portion and the second finger portion being conjoined at the respective second ends, the first finger portion being larger than the second finger portion, the plinth-like body having a contact face and an attachment face;
- means positioned on the attachment face of the first finger portion for attaching the plinth-like body to an haemostatic compression device;
- a channel positioned between the first finger portion and the second finger portion, the channel extending inwardly from the respective first ends of the first finger portion and the second finger portion and terminating at the conjoined respective second ends, the channel passing through the plinth-like body from the contact face to the attachment face; and
- an arrow positioned on the attachment face of the first finger portion, the arrow extending away from the second finger portion substantially perpendicularly to the channel, thereby assisting health care professionals in positioning the plinth-like body;

thirdly, attaching the haemostatic pressure pad to the haemostatic compression device;

fourthly, positioning the contact face of the haemostatic pressure pad on a leg of a patient with the wound positioned between the sidewalls of the channel and the arrow pointing toward the patient's umbilicus, then using the haemostatic compression device to apply sufficient force to staunch blood flow, the channel extending substantially perpendicularly to both a femoral artery and a femoral vein in the leg of the patient with the first finger portion staunching blood flow from the heart through the femoral artery and the second finger portion staunching blood flow along the femoral vein back to the heart.

4. In combination:

an haemostatic compression device having a piston with a key shaped terminus; and a haemostatic pressure pad, comprising:
- a plinth-like body including a first finger portion having a first end and a second end, a second finger portion having a first end and a second end, the first finger portion and the second finger portion being conjoined at the respective second ends, the first finger portion being larger than the second finger portion, the plinth-like body having a contact face and an attachment face;
- a boss having a key hole shaped aperture positioned on the attachment face of the first finger portion, such that the key shaped terminus of the piston from the haemostatic compression device is insertable into the key hole shaped aperture to attach the plinth-like body to an haemostatic compression device; and
- a channel positioned between the first finger portion and the second finger portion, the channel extending inwardly from the respective first ends of the first finger portion and the second finger portion and terminating at the conjoined respective second ends, the channel passing through the plinth-like body from the contact face to the attachment face.

5. A haemostatic pressure pad comprising:

a body having first and second finger portions, each finger portion having first and second ends, the finger portions being conjoined at their second ends, the first finger portion being larger than the second finger portion, said finger portions having an upper attachment face and a lower contact face;

said finger portions forming a channel between them extending inwardly from their first ends and extending through the body;

said first finger portion attachment face having a boss, forming a key hole-shaped aperture, protruding upwardly therefrom for attaching the body with a haemostatic compression device.

6. The haemostatic pressure pad as defined in claim 5, wherein an arrow is positioned on the attachment face of the first finger portion, the arrow extending away from the second finger portion substantially perpendicularly to the channel, thereby assisting health care professionals in positioning the body.

* * * * *